United States Patent [19]

Vaillancourt et al.

[11] Patent Number: 5,509,912
[45] Date of Patent: Apr. 23, 1996

[54] CONNECTOR

[75] Inventors: Vincent L. Vaillancourt, Livingson; John J. Welter, Ocean, both of N.J.

[73] Assignee: VLV Associates, East Hanover, N.J.

[21] Appl. No.: 365,900

[22] Filed: Dec. 29, 1994

Related U.S. Application Data

[63] Continuation-in-part of Ser. No. 328,045, Oct. 24, 1994.
[51] Int. Cl.⁶ .................................................. A61M 5/00
[52] U.S. Cl. ........................... 604/283; 604/88; 604/411; 604/905
[58] Field of Search ................................. 604/263, 264, 604/175, 85, 86, 88, 91, 411, 414, 905, 280, 283

[56] References Cited

U.S. PATENT DOCUMENTS 4,645,494  2/1987  Lee et al. ................. 604/175
4,683,916  8/1987  Raines ...................... 137/854
5,306,243  4/1994  Bonaldo .................... 604/86
5,342,326  8/1994  Peppel ...................... 604/284
5,380,306  1/1995  Brinon ...................... 604/244

FOREIGN PATENT DOCUMENTS

WO93/11828  6/1993  WIPO .

*Primary Examiner*—John D. Yasko
*Attorney, Agent, or Firm*—McAulay Fisher Nissen Goldberg & Kiel

[57] ABSTRACT

A female luer connector for intravascular or urological use is provided with a needle having a closed distal end with an opening in the side of the needle. In addition, the needle is sealingly received within a recess of a rubber septum with an interference fit between the distal end of the needle and the septum. A slit may be formed in the septum to facilitate penetration of the needle through the septum when in use. In one embodiment, the septum has an elongated recess so that the needle may be received under compression in one portion for storage purposes and in a second portion when in use.

33 Claims, 5 Drawing Sheets

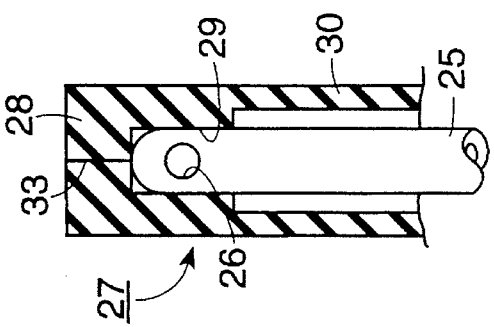
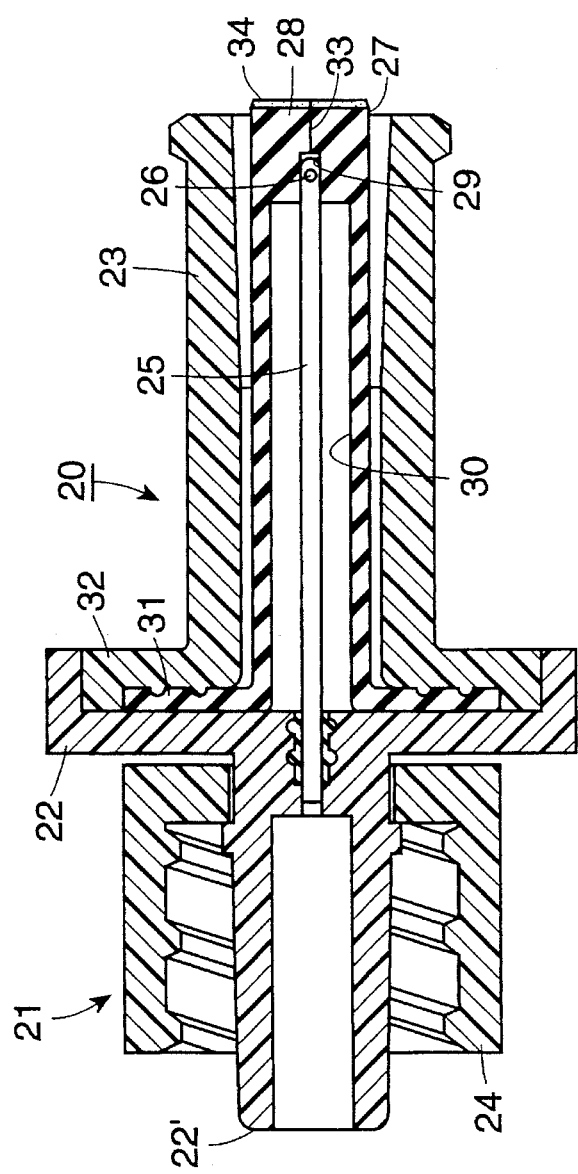

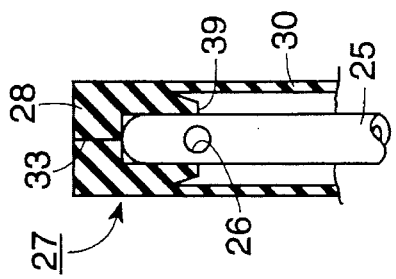
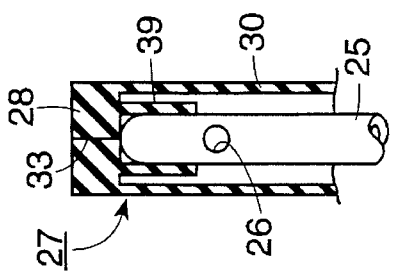
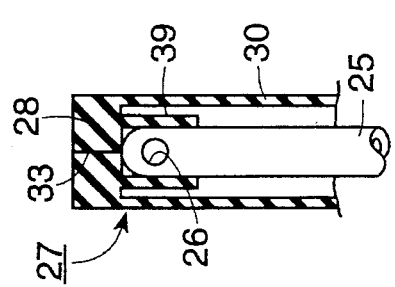
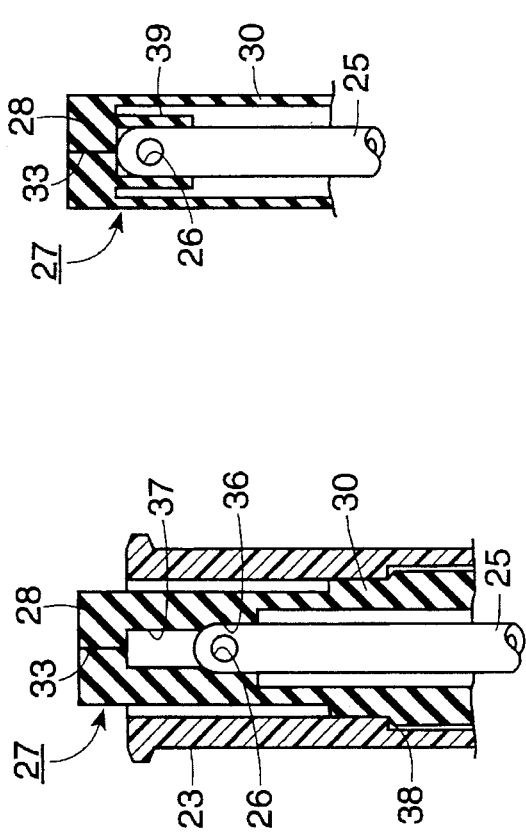

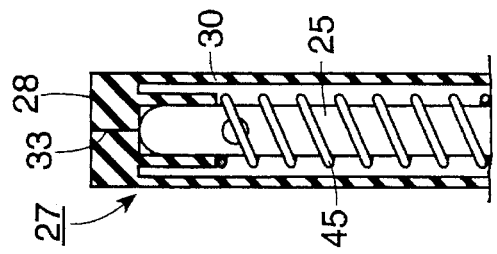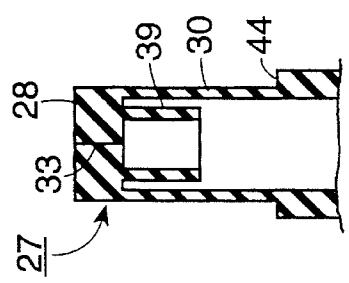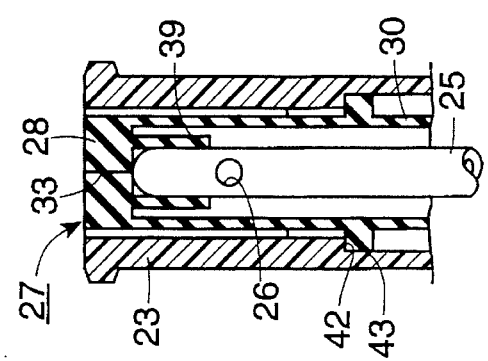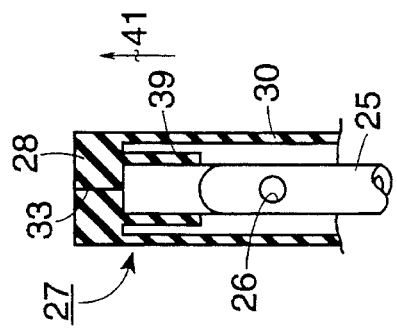

CONNECTOR

This is a continuation-in-part application of pending U.S. patent application Ser. No. 08/328,045, filed Oct. 24, 1994.

This invention relates to a connector. More particularly, this invention relates to a septum luer connector for intravascular or urological use.

Heretofore, various types of connectors have been known, for example, for intravascular and urological use, wherein a hollow needle is disposed within a collapsible tube having a rubber septum at a distal end positioned coaxially of the needle. Where such a connector has been made as a female luer connector, use has been made of a male luer connector or the like to engage with and to push the septum back over the needle thereby exposing the needle. During this time, the needle pierces through the septum and enters into the male luer connector thereby establishing communication therewith. Connectors employing such constructions are described in U.S. Pat. No. 5,122,123.

One of the concerns with the above types of connectors has been the possibility that repeated piercing of the septum, which is usually made of rubber, in more or less one location may allow leakage through the septum after the septum has been returned to an extended position spaced from the hollow needle. This is particularly due to the fact that the thickness of the septum is limited. As a result, the potential resistance to a high pressure is limited.

In order to minimize the concern concerning leaking, use has been made of a compression ring about the septum so that a preload is placed upon the septum in order to ensure a self-sealing of the septum after the septum has been slid off a needle when returning to an extended position.

Another concern which has arisen with respect to septum luer connectors of this type has been the potential for slivering of the septum by the needle. That is, during penetration of the septum by the hollow needle, there is a risk that a sharp needle will cut out a small sliver from the male luer connector and allow the sliver to pass into the blood flow of a patient. This concern can be overcome by slightly bending the tip of the needle inwardly.

Accordingly, it is an object of the invention to provide a septum luer connector which has a minimal risk of leakage.

It is another object of the invention to eliminate slivering of a male luer connector by a needle passing through the septum.

Briefly, the invention provides a connector which is comprised of a hollow needle having a closed distal end with at least one opening in a side of the distal end for passage of fluid and a septum receiving the hollow needle therein in sealed relation. In particular, the septum is provided with a wall closing the end and a recess which slidably receives the closed end of the hollow needle. In addition, the septum and needle are relatively movable with respect to each other in order to permit passage of the distal end of the needle through the distal end of the septum.

In one embodiment, the septum may be provided with a slit to facilitate the passage of the hollow needle. In another embodiment, the septum may be of solid construction, that is, without a slit. In this latter embodiment, the needle may be provided with a spike end or the like which is able to pierce through the septum.

The septum may be made of any suitable material and preferably rubber. Further, the septum may include a tubular portion which extends proximally from the septum and which is collapsible at least in one portion in order to permit the wall of the septum to pass over the distal end of the needle.

In one embodiment, the opening in the needle is sealingly received within the recess of the septum for example with an interference fit between the needle and the septum. In this embodiment, any fluid seeking to escape from the needle must therefore pass through the opening in the side of the needle and must force the inner wall of the septum to expand sufficiently to allow the fluid to pass between the needle and septum to the outside of the septum. By controlling the amount of the interference fit between the septum and the needle, the leakage pressure can be increased or decreased.

In another embodiment, the opening in the needle may be partially received in sealed relation within the recess of the septum whereas in another embodiment, the opening may be spaced longitudinally from the recess of the septum.

In still another embodiment, a compression ring may be concentrically mounted on the septum in order to circumferentially compress the wall of the septum. The compression ring thus serves to significantly increase the leakage pressure at relatively low interference fits. By encapsulating the septum in the compression ring, it becomes virtually impossible for the septum to flow, i.e. to relieve the compressive force thereon. As a result, the initial sealing characteristics may be retained over a relatively long period of time.

In another embodiment, the septum is provided with two internal annular portions in order to slidably receive the needle in sealed relation for different purposes. For example, the septum includes a first annular portion for slidably receiving the distal end of the needle for storage purposes and a second annular portion farther along towards the distal end of the septum. Both annular portions are of the same inside diameter; however, the second annular portion may have an inside diameter which is less than the inside diameter of the first annular portion in order to slidably receive the needle in sealed relation at a time of use. In this respect, the distal end of the needle is sealingly engaged only within the first annular portion for storage purposes. Thus, over time, any set in the material of the rubber septum due to the circumferential expansion of the septum in this area does not interfere with the subsequent need to have a reliable seal when in use. Should one desire to use the connector, the septum is pushed inwardly of the connector so as to move the distal end of the needle from within the first annular portion which may have stretched or set over time into the second annular portion which has remained unstressed during storage. At the time of use and not before, the entire rubber septum is placed under normal compression in order to achieve the desired properties. At most, the connector should only maintain these forces for only a few days as opposed to months and even years (in storage) prior to use and at storage temperatures. In addition, a compression ring may be concentrically mounted on the second annular portion of the septum in order to circumferentially compress this second annular portion.

In still another embodiment, the connector may be provided with a rigid tubular housing part to receive the septum concentrically therein. In this embodiment, the housing part may be provided with an internal annular recess in order to receive a longitudinally collapsed portion of the tubular portion of the septum in locking relation in response to movement of the second annular portion of the septum over the distal end of the needle. That is, when the septum is collapsed so as to move from the position of storage wherein the distal end of the needle is sealingly engaged within the first annular portion to the position of use in which the second annular portion receives the needle, the collapsed portion of the tubular portion is received within the annular recess of the housing part in a locked relationship so as to prevent a return motion of the septum, i.e. extension of the septum relative to the needle.

In still another embodiment, an inner annular wall extends from the septum in spaced concentric relation to the outer wall to receive the distal end of the needle in seal tight relation. In addition, the opening of the needle may be disposed within the plane of the inner annular wall or may be disposed completely outside the inner annular wall or only partially within and partially outside the inner annular wall. In this embodiment, where the opening is not completely sealed over, fluid may flow through the needle into the surrounding tubular portion and into the space between the two concentric walls. In this way, the pressure of the fluid within the collapsible tubular part serves to increase the sealing pressure on the distal end of the needle via the inner wall. One advantage of this embodiment is that the same seal leakage properties can be obtained as in the other embodiments with much less of an interference fit between the needle and the rubber septum.

It has been found that the collapsible tubular portion longitudinally elongates under an internal pressure. When the elongation of the tubular portion is sufficient that the needle no longer is fully engaged with the septum, the connector may begin to leak. Specifically, leakage takes place through the slit in the septum. Accordingly, in another embodiment, a means is provided for preventing longitudinal stretching of the collapsible tubular portion under an internal pressure to a degree at which the septum is no longer maintained on the needle in sealed relation. By way of example, such a means includes an internal shoulder on the rigid tubular part of the connector and an external annular ring on the collapsible tubular portion for abutting the shoulder in an extended position of the collapsible tubular portion, i.e. in a stretched condition. In this way, the pressure required to initiate leakage is substantially increased. In addition, upon removal of the internal pressure, the septum retracts unto the needle so that the connector behaves in the normal manner.

Studies have shown that for higher Durometer (more rigid) septums, higher leakage pressures can be obtained. This is due to the mechanism of failure, that is, elongation of the collapsible tubular portion as well as to the fact that the septum becomes more difficult to stretch when the Durometer is increased. In this respect, silicone rubber appears to be the material of choice rather than a synthetic latex free rubber.

The connector may be constructed so that the septum projects slightly beyond the tubular housing part. In this position, the face of the septum is exposed so that the face can be wiped prior to use with a suitable material to remove and/or kill bacteria. Also, the septum may be positioned flush with the housing part. In the alternative, a coating or a deposit, such as of silver or anti-microbial material may be applied on the face of the septum. In this latter case, there should be no need to swab the septum prior to use.

It has also been found that a condition can exist in an IV line in which there is a negative pressure on the downstream side of a female luer septum when a male luer adaptor is not engaged. Where a conventional type connector is employed, there is a real concern that air may enter the connector by way of the slit in the top of the septum. The connector of the present invention overcomes this problem. In this respect, when a negative pressure is introduced at a downstream point, the sealing properties of the connector actually tend to increase. As a result, the danger of air entering into the connector is further minimized.

These and other objects and advantages of the invention will become more apparent from the following detailed description taken in conjunction with the accompanying drawings wherein:

Fig. 1 illustrates a cross-sectional view of a female luer connector constructed in accordance with the invention;

FIG. 2 illustrates a partial cross sectional view of the septum of FIG. 1 having the hollow needle sealing received therein in accordance with the invention;

Figure 6:
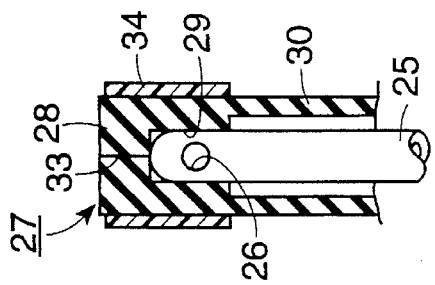
FIG. 6 illustrates a second embodiment of a connector employing a compression ring about the septum in accordance with the invention.
Figure 10:
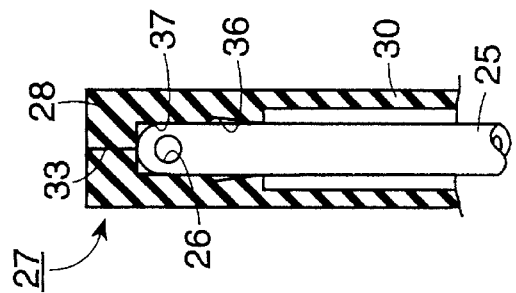
Figure 9:
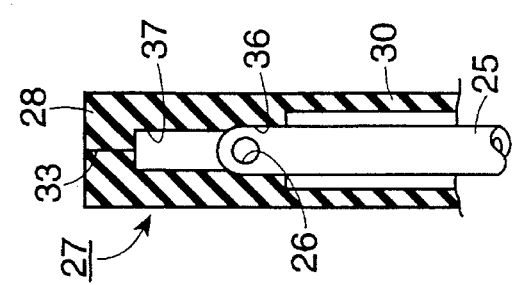
Figure 8:
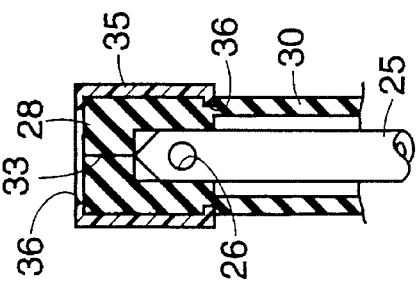
Figure 7:
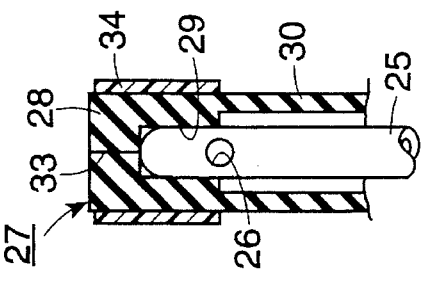

Fig, 7 illustrates a view similar to FIG. 6 of an embodiment having a hollow needle with an opening partially sealed by the septum in a position of use;

FIG. 8 illustrates a modified connector employing a compression ring of encapsulating type in accordance with the invention;

Fig, 9 illustrates a further embodiment of a connector employing a stepped septum with two annular sealing portions in accordance with the invention;

FIG. 10 illustrates a view of the connector of FIG. 9 with the hollow needle in a position of use;

FIG. 11 illustrates a further embodiment having a rigid tubular part surrounding the longitudinally collapsible septum with a recess in the tubular part to receive a collapsed portion of the septum in accordance with the invention;

FIG. 12 illustrates a further embodiment in which an inner annular wall extending from a septum sealingly receives a hollow needle in accordance with the invention;

FIG. 13 illustrates a view similar to Fig, 12 of an embodiment wherein the needle has an opening spaced from the annular wall extending from the septum;

FIG. 14 illustrates a structure similar to FIG. 13 with a modified inner wall sealingly receiving a hollow needle with an opening in the side wall;

FIG. 15 illustrates a partial cross-sectional view of a septum of FIG. 1 in which the collapsible tubular portion has stretched under an internal pressure;

FIG. 16 illustrates a view similar to FIG. 15 employing a means for preventing longitudinal stretching of the collapsible tubular portion in accordance with the invention;

FIG. 17 illustrates an alternative construction for preventing longitudinally stretching of the collapsible tubular portion; and FIG. 18 illustrates a modified cross-sectional view of a female connector employing a spring for biasing the septum into an extended position in accordance with the invention.

Referring to FIG. 1, the female connector 20, e.g. a conventional female luer connector, is constructed in a conventional manner with a housing 21, e.g. of a plastic material, having a hub 22 and a rigid tubular part 23 extending from the hub 22. Also, the hub 22 has a rigid tubular part 22' extending from the hub 22 which is concentrically surrounded by an internally threaded collar 24 or the like to form a male luer connection so as to threadably receive a luer connector on an IV line or the like (not shown).

In addition, as shown in FIG. 1, a hollow needle 25 is mounted in the hub 22 concentrically within the tubular portion 23 for conveying fluid therethrough to opposite sides of the hub 22. This needle 25 has a closed distal end a blunt rounded end and at least one opening 26 in a side of the distal end for the passage of fluid. For example, the needle 25 has a pair of openings 26, each opposite the other. Still further, a septum 27, for example of rubber or other suitable material is secured within the tubular portion 23 of the housing 21 to receive the needle 25 in sealed relation. As shown, this septum 27 has a transverse wall 28 closing the end and a recess 29 which slidably receives the closed end of the needle 25 in an interference fit relation. The septum 27 is integral with a longitudinally collapsible tubular portion 30 which extends within the tubular part 23 of the housing 21 in order to seal off the needle 25 and to permit movement of the septum 27 over the needle 25 to expose the opening in the needle. The collapsible tubular portion 30 includes a flange 31 which is sandwiched between the hub 22 and a flange 32 on the tubular portion 23 to hold the collapsible tubular portion 30 in place.

By way of example, the needle 25 has an outside diameter of 0.042 inches while each opening 26 has a diameter of 0.025 inches. The recess 28 in the septum 27 has a diameter of 0.038 inches so as to provide an interference fit of 0.004 inches.

As indicated in FIG. 1, the septum 26 has a slit 33 in the distal end which is aligned with the needle 25 in order to facilitate passage of the needle 25 through the septum 27.

As shown in FIGS. 1 and 2, the opening 26 in the needle 25 is sealingly received within the septum 27 when the connector 20 is ready for use. In this way, the interference fit between the septum 27 and the needle 25 serves to seal the opening 26 against the passage of fluid. In this respect, in order to have any leakage through the opening 26 of the needle 25, the pressure within the needle 25 must be sufficiently large to cause a bulging out of the septum 27 away from the needle 25 so as to permit a leakage path between the needle 25 and the septum 27 for the fluid. By controlling the amount of interference fit between the septum 27 and the needle 25, the leakage pressure may be increased or decreased.

Referring to FIG. 1, when the connector 20 is to be used, a line (not shown) is connected to the male luer connection 22',24 in a conventional manner. Next, the exposed face of the septum 27 is swabbed in order to remove and/or kill bacteria or the like thereon. Alternatively, a coating 34, such as a silver coating or an anti-microbial coating, may be formed on the face of the septum 27 to eliminate the need for swabbing of the septum face, Thereafter, a male luer connector (not shown) or other type of adaptor is pushed against the face of the septum 27 to push the septum 27 over the needle 25 and into the rigid tubular portion 23 of the connector 20 in a conventional manner. The septum 27, thus, slides along the outer surface of the needle 25 until the opening 26 is exposed to the interior of the male luer connector or adaptor.

Once the male luer connector or adaptor is removed from the female luer connector 20, the bias in the collapsed tubular portion 30 pushes the septum 27 back over the needle 25 into the extended position shown in FIG. 1 wherein the end of the needle 25 is again spaced from the wall 28 of the septum 27 and held in interference fit relation within the recess 29 of the septum 27. At this time, the opening 26 in the needle 25 is sealed by the septum 27 so leakage of fluid from the needle 25 is prevented.

Figure 3:
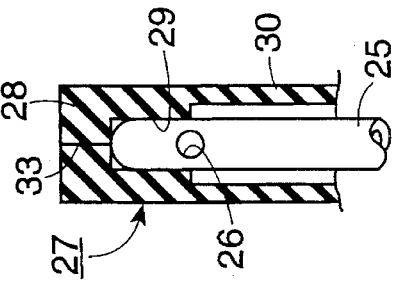
FIG. 3 illustrates a view similar to FIG. 2 with a hollow needle having an opening in the side which is partially sealed by the septum in accordance with the invention.

Referring to FIG. 3, wherein like reference characters indicate like parts as above, the opening 26 in the needle 25 may be disposed so as to be partially sealed by the septum 27 when the needle 25 is received within the septum 27. In this embodiment, fluid may pass from the hollow needle 25 through the unexposed part of the opening 26 into the interior of the collapsible tubular portion 30. However, the interference fit between the needle 25 and the septum 27 serves to seal off the interior of the collapsible tubular portion 30 from the outside environment.

Figure 4:
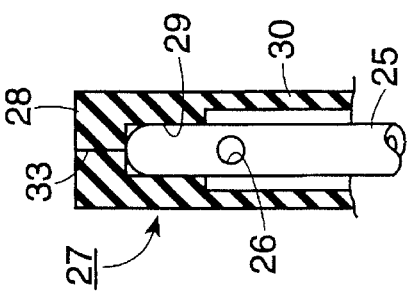
FIG. 4 illustrates a view similar to FIG. 2 wherein the needle has an opening which is spaced from the septum in accordance with the invention.

Referring to FIG. 4, the opening 26 in the needle 25 may alternatively be positioned so as to be completely exposed when the needle 25 is seated within the septum 27. Again, fluid within the needle 25 may pass through the opening 26 into the interior of the collapsible tubular portion 30 but is sealed off from the outside environment.

Figure 5:
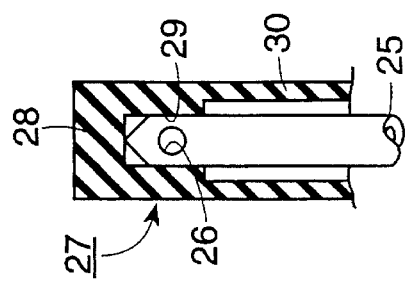
FIG. 5 illustrates a view similar to FIG. 2 of a septum which is not preslit.

Referring to FIG. 5, the septum 27 may also be formed without any slit. In this case, the needle 25 may be provided with a spike-type shape to facilitate piercing of the wall 28 of the septum 27.

Referring to FIG. 6, wherein like reference characters indicate like parts as above, the connector may be provided with a compression ring 34 around the septum 27 in order to circumferentially compress the wall 28 of the septum 27. In this manner, the leakage pressure can be increased and/or the compression ring 34 serves to minimize the effects of septum 27 compression set with time and temperature.

Referring to FIG. 8, wherein like reference characters indicate like parts as above, the compression ring 35 may be modified so as to have inwardly directly flanges 36 at each end so as to encapsulate the septum therein.

Referring to FIGS. 9 and 10, wherein like reference characters indicate like parts as above, the septum 27 may be formed with a first annular portion 36 to slidably receive the needle 25 in sealed relation for storage purposes and a second annular portion 37 in order to slidably receive the needle 25 in sealed relation at a time of use (FIG. 10). In this embodiment, the recess within the septum 27 is made of a uniform diameter, e.g. 0.028 inches, but is of a length to accommodate the needle 25 in two positions, i.e. a storage position in which the needle 25 is received only near the mouth of the recess and a use position in which the needle 25 is received fully within the recess. Further, any set which takes place in this portion 36 during storage, for example over a period of months, due to expansion of the portion does not subsequently effect the sealing characteristics of the connector as the second annular portion 37 remains unstretched and unstressed.

When the connector is to be used, the septum 27 is slid proximally relative to the needle 25 so as to bring the needle 25 within the second annular portion 37 which has remained unstressed during storage thereby allowing the interference fit to effect a sealing relation between the needle 25 and the septum 27. In this condition of use (FIG. 10), the connector serves to maintain a seal against higher pressures which exist in use.

Referring to FIG. 11, the rigid tubular portion 23 of the housing 21 is provided with an interior annular recess 38 in order to receive a longitudinally collapsed portion of the tubular portion 30 in locking relation in response to movement of the second annular portion 37 of the septum 27 over the distal end of the needle 25, In this way, once the septum 27 has been pushed back over the needle 25, for example into the position shown in FIG. 10, a return of the septum 27 to the extended position shown in Fig. 9 is prevented. That is, the collapsed portion of the tubular portion 30 is received in the recess 38 of the housing portion 23 in a locked manner whereby the septum 27 cannot be returned to the fully extended position. Subsequent collapsing of the tubular portion 30 is, however, permitted with a subsequent extension of the tubular portion 30 to the condition shown in FIG. 10. Alternatively, a suitable stop means (not shown) may be provided on the outside of the collapsible rubber tubular portion 30 to engage in the internal recess 38 in the rigid housing portion 23 to preclude a return of the septum 27 to the storage position of Fig. 9.

Referring to FIG. 12, wherein like reference characters indicate like parts as above, the septum 27 may have an integral inner annular wall 39 extending therefrom in spaced concentric relation to the collapsible tubular portion 30 (outer wall). As shown, this inner annular wall 39 receives the distal end of the needle 25 while completely covering over the opening 26 in the needle 25.

Alternatively, as shown in FIG. 13, the opening 26 in the needle 25 may be disposed in spaced relation to the inner wall 39. In this case, fluid within the hollow needle 25 may pass into the collapsible tubular portion 28 to surround the inner annular wall 39 thereby increasing the sealing pressure on the inner wall 39 against the hollow needle 25. In this embodiment, less of an interference fit is required between the needle 25 and inner annular wall 39 than in other embodiments due to the additional sealing pressure created by the fluid within the tubular portion 30 and about the inner annular wall 39.

Referring to FIG. 14, wherein like reference characters indicate like parts as above, the inner annular wall 39 may have a tapered outer surface 40 so as to define a gap between the inner wall 39 and tubular portion 30. Again, fluid from within the hollow needle 25 may pass within this annular gap so as to press the inner wall 39 circumferentially about the needle 25 to increase the sealing effect of the septum 27 on the needle 25.

In the event that the line to which the female luer connector 20 is connected is under negative pressure, there is an increase in the sealing effect between the septum 27 and the needle 25 so as to further preclude the risk that air may enter into the needle 25 from the outside environment.

Referring to FIG. 15, wherein like reference characters indicate like parts as above, should the internal pressure within the collapsible portion 30 increase, the collapsible portion 30 stretches in a distal direction as indicated by the arrow 41, i.e. the tubular portion elongates. Depending upon the internal pressure, the elongation of the tubular portion 30 may be sufficient to have the annular wall 39 of the septum 27 disengage from the end of the needle 25 so that fluid under pressure enters into the space defined by the inner wall 39. Depending upon the pressure, leakage may occur through the slit 33. In order to eliminate this problem, a means is provided for preventing longitudinal stretching of the collapsible tubular portion 30 under an internal pressure therein beyond a point at which the septum 27 is no longer maintained on the needle 25 in sealed relation. For example, as shown in FIG. 16, wherein like reference characters indicate like parts as above, the means for preventing stretching of the collapsible tubular portion 30 beyond a certain point includes an internal shoulder 42 on the rigid tubular part 23 and an external annular ring 43 on the collapsible tubular portion 30 for abutting the shoulder 42 in an extended position thereof. For example, the annular ring 43 may be integrally formed with the collapsible tubular portion 30. The position of the annular ring 43 is such that stretching of the collapsible tubular portion 30 under an internal pressure is prevented proximally of the ring 43 while stretching of the tubular portion 30 distally of the ring 43 is minimized to an extent that the septum annular wall 39 remains in sealing engagement with the needle 25.

By placing the annular ring 43 on the collapsible tubular portion 30, the pressure required to initiate leakage is substantially increased. In this respect, it has been found that for higher Durometer (i.e. more rigid) septums 27 and tubular portions 30, the amount of internal pressure that can be resisted before leakage occurs increases. That is, the harder the rubber, the less the elongation of the tubular portion 30. Accordingly, silicon rubber appears to be a material choice rather than an synthetic latex free rubber.

Testing has shown that for a rubber Durometer A scale of 30, the leakage pressure occurred in the range of from 25 to 30 psi; for a Durometer A of 40, the pressure and leakage occurred between 55 an 60 psi and for a rubber Durometer A of 50, leakage occurred over 60 psi.

Referring to FIG. 17, the means for preventing longitudinal stretching of the collapsible tubular portion 30 may alternatively include a means such as an external shoulder 44 on the collapsible tubular portion 30 for abutting the internal shoulder 42 (see FIG. 16) on the rigid tubular part 23.

Referring to FIG. 18, in order to ensure that the rubber septum 27 immediately returns to the extended position of rest, for example, upon withdrawal of a male adaptor, a spring 45 is provided concentric to the needle 25 and the tubular portion 30 for biasing the septum 27 distally of the needle 25 to cause the wall 28 of the septum 27 to move distally along the needle 25. This spring 45 may be anchored at the proximal end to a fixed part of the connector 20 such as the hub 22 of FIG. 1 or may be embedded in the tubular portion 30 integral with the septum 27.

The invention thus provides a female luer connector for intravascular or urological use in which a needle can be held in a reliable seal-tight relation with a substantial reduction in the risk of leakage until ready for use.

Further, the invention provides a female luer connector in which the potential risk of slivering of a male luer connector by a sharpened of a needle is eliminated since a sharp end is eliminated from the tip of the needle used to pass through the septum.

What is claimed is:

1. A connector for intravascular and urological use comprising a hollow needle having a closed rounded distal end and at least one opening in a side of said distal end for passage of fluid; and a septum receiving said hollow needle therein in sealed relation, said septum having a transverse wall and a recess slidably receiving said closed end of said hollow needle, said septum and said needle being relatively movable to permit passage of said distal end of said needle through said wall of said septum.

2. A connector as set forth in claim 1 which further comprises a tubular portion extending proximally from said septum, said tubular portion being collapsible at least in one portion thereof to permit said wall of said septum to pass over said distal end of said needle.

3. A connector as set forth in claim 1 wherein said septum wall has a slit aligned with said needle to facilitate passage of said needle through said wall.

4. A connector as set forth in claim 3 wherein said needle is received in said recess of said septum with an interference fit.

5. A connector as set forth in claim 4 wherein said opening in said needle is sealingly received within said recess wall of said septum.

6. A connector as set forth in claim 4 wherein said opening in said needle is partially received in sealing relation within said recess of said septum.

7. A connector as set forth in claim 4 wherein said opening in said needle is spaced longitudinally from said recess of said septum with said distal end of said needle received in said recess of said septum.

8. A connector as set forth in claim 3 which further comprises a compression ring concentrically mounted on said septum to circumferentially compress said wall of said septum.

9. A connector as set forth in claim 1 wherein said recess includes a first annular portion to slidably receive said needle in sealed relation for storage purposes and a second annular portion to slidably receive said needle in sealed relation at a time of use.

10. A connector as set forth in claim 9 wherein said septum has a slit in said wall aligned with said needle to facilitate passage of said needle through said wall.

11. A connector as set forth in claim 9 which further comprises a compression ring concentrically mounted on said second annular portion of said septum to circumferentially compress said second annular portion.

12. A connector as set forth in claim 9 which further comprises a tubular portion extending proximally from said septum, said tubular portion being longitudinally collapsible to permit said septum to move relative to said needle.

13. A connector as set forth in claim 2 which further comprises a rigid tubular housing part receiving said septum concentrically therein, said housing part having an annular recess to receive a longitudinally collapsed portion of said tubular portion in locking relation in response to movement of said second annular portion of said septum over said distal end of said needle.

14. A connector as set forth in claim 2 wherein said septum has an integral inner annular wall in spaced concentric relation to said collapsible tubular portion, said inner annular wall receiving said distal end of said needle.

15. A connector as set forth in claim 14 wherein said opening of said needle is disposed within said inner annular wall of said septum with said needle being sealed within said inner wall.

16. A connector as set forth in claim 14 wherein said opening of said needle is disposed outside said inner annular wall with said needle being sealed within said inner wall.

17. A connector as set forth in claim 14 wherein said opening of said needle is disposed partially within and partially outside said inner annular wall of said septum with said needle being sealed within said septum.

18. A connector as set forth in claim 14 wherein said inner annular wall has a tapered outer surface merging into said tubular portion to define an annular recess for receiving fluid under pressure from said needle.

19. A connector as set forth in claim 2 which further comprises a spring concentric to said needle and said tubular portion for biasing said septum distally of said needle to cause said wall of said septum to move distally along said needle.

20. A female connector comprising a rigid tubular housing part having an internal shoulder;

a hollow needle disposed concentrically within said housing part and in fixed relation thereto, said needle having a closed distal end and at least one opening in a side of said distal end for passage of fluid;

a rubber septum receiving said distal end of said needle in sealed relation;

a longitudinally collapsible tubular portion extending from said septum within and spaced from said housing part to permit movement of said septum along said needle to allow said needle to pierce said septum to expose said opening in said needle; and means on said collapsible tubular portion for abutting said internal shoulder of said rigid tubular housing part to prevent stretching of said collapsible tubular portion under an internal pressure therein beyond a point at which said septum is no longer maintained on said needle in sealed relation.

21. A connector as set forth in claim 20 which further comprises a spring concentric to said needle and said tubular portion for biasing said septum distally of said tubular portion from a collapsed position of said tubular portion.

22. A female connector comprising a housing having a hub and a rigid tubular part extending from said hub;

a hollow needle mounted in said hub for conveying fluid therethrough to opposite sides of said hub, said needle having a closed distal end and at least one opening in a side of said distal end for passage of fluid;

a rubber septum within said housing and receiving said needle therein in sealed relation, said septum having a wall at one end and a recess slidably receiving said closed end of said needle in an interference fit relation; and a longitudinally collapsible tubular portion extending from said septum within said tubular part of said housing to permit movement of said septum over said needle to expose said opening in said needle.

23. A female connector as set forth in claim 22 wherein said septum has a slit in said wall aligned with said needle to facilitate passage of said needle through said septum.

24. A female connector as set forth in claim 22 wherein said opening in said needle is sealingly received within said recess of said septum with said needle positioned in said recess of said septum.

25. A female connector as set forth in claim 22 which further comprises a compression ring concentrically mounted on said septum to circumferentially compress said wall of said septum.

26. A female connector as set forth in claim 22 wherein said septum includes a first annular portion to slidably receive said needle in sealed relation for storage purposes and a second annular portion to slidably receive said needle in sealed relation at a time of use.

27. A female connector as set forth in claim 26 wherein said housing part has an internal recess to receive a longitudinally collapsed portion of said tubular portion in locking relation in response to movement of said second annular portion of said septum over said distal end of said needle.

28. A female connector as set forth in claim 22 wherein said septum has an integral inner annular wall extending therefrom in spaced concentric relation to said collapsible tubular portion, said inner annular wall receiving said distal end of said needle.

29. A female connector as set forth in claim 22 wherein said housing has a male luer connection extending from said hub on a side opposite from said septum.

30. A female connector as set forth in claim 22 further comprising a coating or deposit of silver or other antimicrobial material on an exposed face of said wall of said septum.

31. A female connector as set forth in claim 22 further comprising means for preventing longitudinal stretching of said collapsible tubular portion under an internal pressure therein to a degree at which said septum is no longer maintained on said needle in sealed relation.

32. A female connector as set forth in claim 31 wherein said means includes an internal shoulder on said rigid tubular part and an external annular ring on said collapsible tubular portion for abutting said shoulder in an extended position thereof.

33. A female connector as set forth in claim 31 wherein said means includes an internal shoulder on said rigid tubular part and an external shoulder on said collapsible tubular portion for abutting said internal shoulder.

* * * * *